United States Patent [19]
Fitz

[11] Patent Number: 6,014,588
[45] Date of Patent: Jan. 11, 2000

[54] FACET JOINT PAIN RELIEF METHOD AND APPARATUS

[76] Inventor: William R. Fitz, 6500 Mariemont Ave., Cincinnati, Ohio 45227

[21] Appl. No.: 09/056,216

[22] Filed: Apr. 7, 1998

[51] Int. Cl.[7] ................................. A61N 1/18; A61N 1/34
[52] U.S. Cl. ............................................... 607/46; 607/43
[58] Field of Search ......................................... 607/43, 46

[56] References Cited

U.S. PATENT DOCUMENTS

| | | | |
|---|---|---|---|
| 4,044,774 | 8/1977 | Corbin et al. | 128/404 |
| 4,411,258 | 10/1983 | Pujals, Jr. | 128/60 |
| 4,570,640 | 2/1986 | Barsa . | |
| 4,633,889 | 1/1987 | Talalla et al. | 128/784 |
| 4,803,986 | 2/1989 | Dufresne et al. | 128/385 |
| 5,031,618 | 7/1991 | Mullett | 128/421 |
| 5,041,974 | 8/1991 | Walker et al. | 364/413.27 |
| 5,196,015 | 3/1993 | Neubardt | 606/61 |
| 5,342,409 | 8/1994 | Mullett | 607/46 |
| 5,358,513 | 10/1994 | Powell, III et al. | 607/48 |
| 5,417,719 | 5/1995 | Hull et al. . | |
| 5,423,877 | 6/1995 | Mackey | 607/117 |
| 5,474,558 | 12/1995 | Neubardt | 606/79 |
| 5,501,703 | 3/1996 | Holshelmer et al. | 607/46 |
| 5,643,330 | 7/1997 | Holsheimer et al. | 607/46 |
| 5,702,429 | 12/1997 | King | 607/46 |
| 5,792,187 | 8/1998 | Adams | 607/46 |

OTHER PUBLICATIONS

R.E. Kinard, MD, "Diagnostic Spinal Injection Procedures," Neurosurgery Clinics of North America, vol. 7, No. 1, Jan. 1996, pp. 151–165.

C.N. Shealy, MD, "Facet Denervation in the Management of Back and Sciatic Pain," Clinical Orthopaedics and Related Research, No. 115, Mar.–Apr. 1976, pp. 157–164.

S.J. Dreyer, MD, P.H. Dreyfuss, MD, "Low Back Pain and the Zygapophysial (Facet) Joints," Arch Phys Med Rehabil, vol. 77, Mar. 1996, pp. 290–300.

R. North, D. Kidd, M. Lee, S. Piantodosi; "A Prospective, Randomized Study of Spinal Cord Simulation vs. Reoperation for Failed Back Surgery Syndrome: Initial Results," World Society for Stereotactic and Functional Neurosurgery, Oct. 1993, pp. 267–272.

K. Kumar, C. Toth, R. Nath, P. Laing; "Epidural Spinal Cord Stimulation for Treatment of Chronic Pain," Aug. 1996, pp. 110–121.

R. Segal, B. Stacey, T. Rudy, S. Baser, J. Markham; "Spinal Cord Stimulation Revisted,"Neurological Research, Jul. 1998, vol. 20, p. 391–6.

J. Turner, J. Loeser, K. Bell; "Spinal Cord Stimulation for Chronic Low Back Pain: A Systematic Literature Synthesis", Neurosurgery, vol. 37, No. 6, Dec. 1995, pp. 1088–1096.

(List continued on next page.)

*Primary Examiner*—William E. Kamm
*Assistant Examiner*—Carl H. Layno
*Attorney, Agent, or Firm*—Gifford, Krass, Groh, Sprinkle, Anderson & Citkowski, PC

[57] ABSTRACT

An apparatus depolarizes the medial branch of the spinal nerve associated with a painful spinal facet joint so as to block pain impulses from reaching the spinal cord. The preferred apparatus includes a neurostimulator and two or more electrodes which carry electrical pulses to the target nerve or nerves. The impulses are intense enough to cause depolarization of a given medial branch and its articular branches, but not so large as to cause depolarization of the spinal cord itself. In the preferred embodiment the stimulator is physically small and battery operated, facilitating implantation underneath the skin. The stimulator includes a controller and appropriate electronics operative to generate electrical impulses tailored to an individual's need for appropriate pain relief in terms of pulse frequency, pulse width, and pulse amplitude. In an alternative embodiment, the stimulator further includes electrodes and electrical circuitry operative to monitor myoelectrical activity generated by the surrounding muscles and modulate the impulses generated by the stimulator to meet the demands of the individual's activity and/or prolong battery life.

7 Claims, 3 Drawing Sheets

OTHER PUBLICATIONS

D. Doleys, K. Olson; "Psychological Assessment and Intervention in Implantable Pain Therapies," Medtronic Brochure.

"Treating Pain Due to Spinal Stenosis with APT Neurostimulation," Medtronic Clinical Case Study.

"Treating Complex Regional Pain Syndrome with APT Neurostimulation," Medtronic Clinical Case Study.

T. Lehmann, D. Russell, K. Spratt, H. Colby, Y. Liu, M. Fairchild, S. Christensen, "Efficacy of Electroacupuncture and TENS in the Rehabilitaion of Chronic Low Back Pain Patients," Dept. of Orthopaedic Surgery, Univ. of Iowa, Dec. 1985, pp. 277–290.

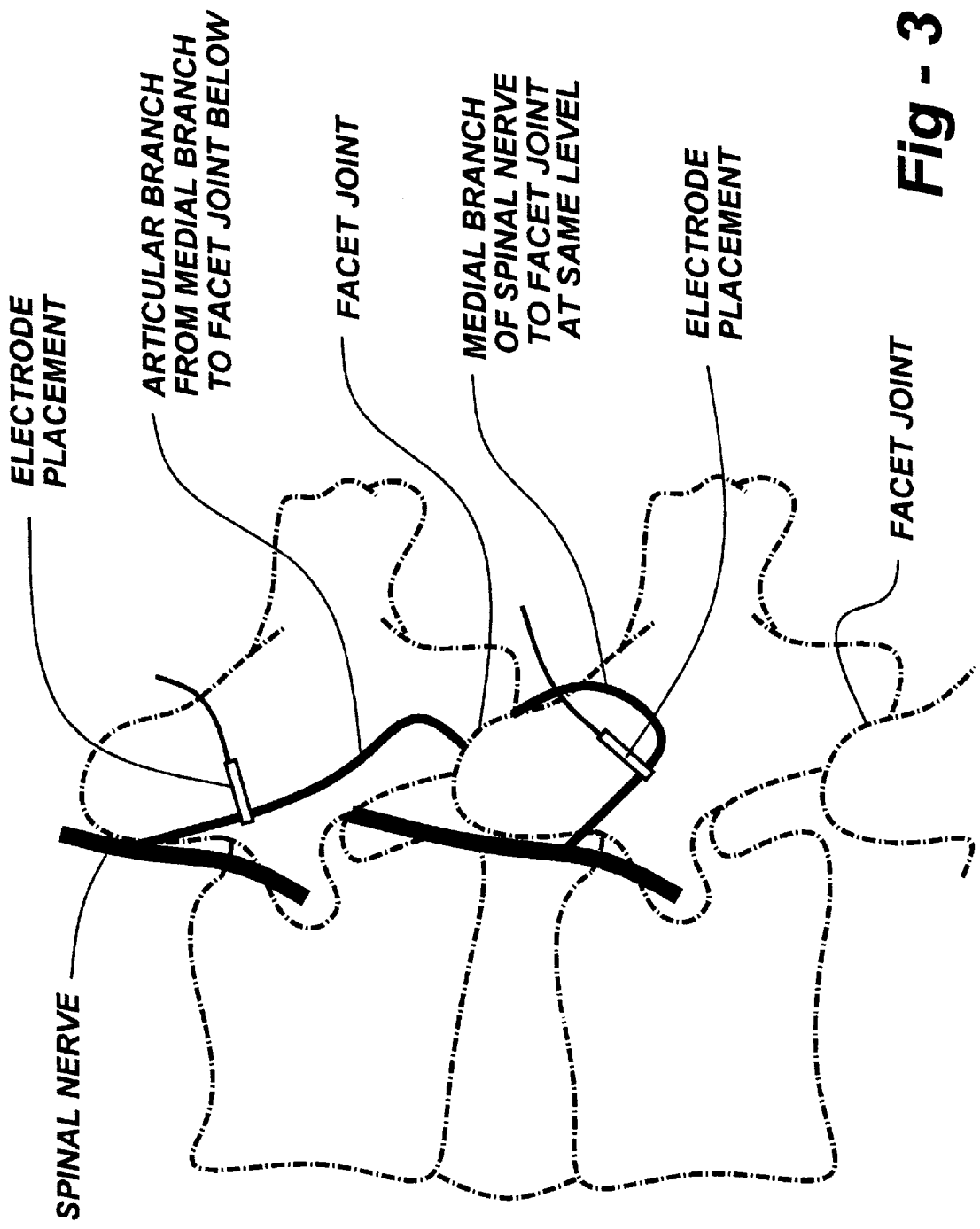

FACET JOINT PAIN RELIEF METHOD AND APPARATUS

FIELD OF THE INVENTION

This invention relates generally to electrically mediated pain relief and, in particular, to the use of electrical current to block sensory pathways associated with the medial branch of the spinal nerve root and its articular branches so as to relieve pain caused by painful zygopophysial joints.

BACKGROUND OF THE INVENTION

A large body of evidence now exists to support the fact that the zygopophysial joints (facet joints) can be pain-producing structures. In particular, has been shown that the facet joints can be a source of chronic spinal pain in the cervical, thoracic and lumbosacral regions. This pain, which can be due to trauma to and/or degeneration of the facet joint, can be disabling in some patients.

Anatomical dissections reveal that the facet joint is innervated by the articular branches of the medial branch of the spinal nerve. Lesioning this nerve has been shown to relieve pain, but regrowth of the nerve is inevitable and pain returns.

Electrical stimulators of other neural structures has been proposed to provide pain relief. U.S. Pat. No. 5,041,974 to Walker et al, entitled MULTICHANNEL STIMULATOR FOR TUNE STIMULATION, includes a user interface enabling the selection of a channel and the creation of a stimulus wave signal. A slave circuit associated with the channel receives the wave building signal and generates a corresponding low-power stimulus. An output circuit coupled to the slave electronically isolates the stimulus from the other channels, amplifying and converting it to produce a high-fidelity stimulus wave signal.

There have also been developed neuro-type stimulators which are responsive to patient conditions, and adjust their function in accordance therewith. For example, in U.S. Pat. No. 5,031,618 to Mullett, entitled POSITION-RESPONSIVE NEURO STIMULATOR, a position sensor such as a mercury switch which may be used to determine whether a patient is erect or supine, is implanted in the patient. This position information is then used to vary stimulation intensity, in terms of pulse amplitude, pulse width, and a number of pulses per second and other factors. The output of the pulse generator is applied to the spinal cord, peripheral nerves and/or targets in the brain with leads in electrodes in a manner consistent with a given medical need.

To applicant's knowledge, however, no such neuro stimulators, whether adaptive or fixed in their operation, have been applied to the specific problem of pain relief relative to the zygopophysal or facet joints. As the '618 patent points out, stimulation of this type has so far been limited to the treatment of chronic intractable pain requiring spinal cord depolarization. Accordingly, one object of this invention is to provide novel apparatus specifically designed to block painful impulses transmitted by the medial branch of the spinal nerve.

Another important object of this invention is to provide such apparatus in the form of an electrical nerve stimulator that is implantable.

It is a related object of this invention to create a pain-relief mechanism and accompanying methodology that is long lasting while being minimally invasive so as to reduce medical complications.

SUMMARY OF THE INVENTION

The present invention resides in methods and apparatus for depolarizing the medial branch of the spinal nerve associated with a painful spinal facet joint so as to block pain impulses from reaching the spinal cord. Broadly, according to an apparatus aspect, the invention is comprised of a neurostimulator and two or more electrodes which carry electrical pulses to the target nerve or nerves. Current is generated from a negative electrode, and multiple negative leads may be needed to block multiple pain-generating medial and articular branch nerves.

In the preferred embodiment, the apparatus is capable of generating electrical impulses of sufficient intensity to cause depolarization of a given medial branch and its articular branches, but not so large as to cause depolarization of the spinal cord itself.

Although the apparatus may be disposed externally of the individual, in the preferred embodiment the stimulator is physically small and battery operated, facilitating implantation underneath the skin. Accordingly, the components of the stimulator and electrodes would preferably be biocompatible and biostable so as not to cause tissue reactions.

The stimulator includes a controller and appropriate electronics operative to generate electrical impulses tailored to an individual's need for appropriate pain relief in terms of pulse frequency, pulse width, and pulse amplitude. In an alternative embodiment, the stimulator further includes electrodes and electrical circuitry operative to monitor myoelectrical activity generated by the surrounding muscles and modulate the impulses generated by the stimulator to meet the demands of the individual's activity and/or prolong battery life.

BRIEF DESCRIPTION OF THE DRAWINGS

FIG. 3 is a diagram of the medial branch of the spinal nerve showing a preferred electrode placement.

DETAILED DESCRIPTION OF THE INVENTION

This invention is directed toward a nerve stimulator operative to stimulate one or more medial branches of spinal nerve roots and/or its articular branches to the zygopophysial joints (facet joints). The articular branches eminate from the medial branch of the spinal nerve and innervate the zygopophysial joints, which have been shown to be a cause of chronic spinal pain.

Broadly, the medial branch stimulator includes an electrical nerve stimulator that could be external though, in the preferred embodiment, would be implanted under the skin. This stimulator is connected to electrodes preferably placed subcutaneously in the region of the medial branch and its articular branches.

The stimulator generates an electrical output that would be set to the individual's needs, for example, in terms of pulse frequency, pulse width, and pulse amplitude. This stimulator would create a continuous electrical stimulus or may also be a demand stimulator that is modulated by the surrounding muscular activity that is activated by the individual. The electrodes come in many forms but one form is a teflon coated wire that has its distal tip denuded of teflon so as to create an open surface for electrical conductivity through the tissues to the target nerve.

Figure 1:
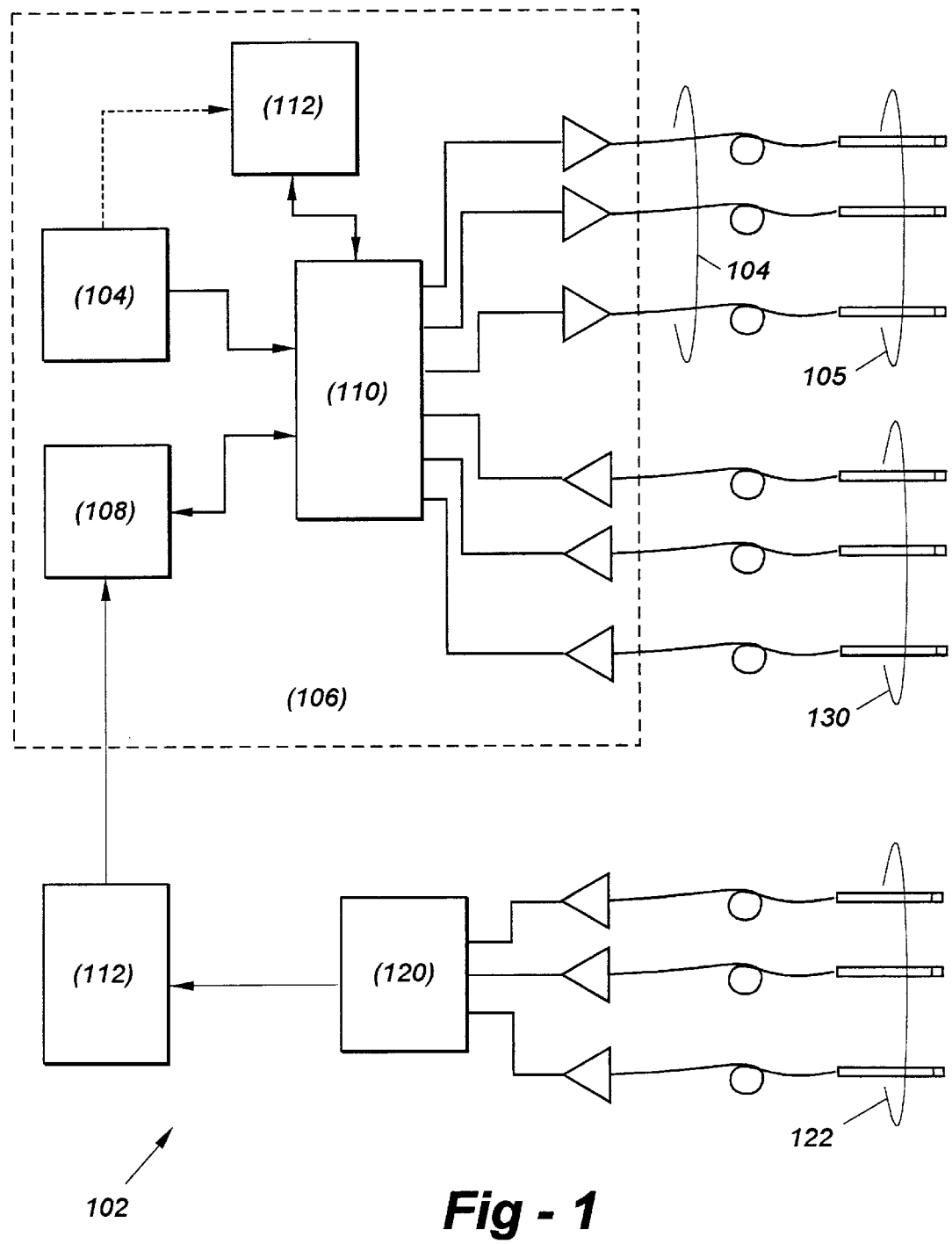
FIG. 1 is a block diagram used to illustrate major electrical subsystems of a stimulator and attachments according to the invention.

As shown in FIG. 1, a preferred apparatus includes a stimulator 102 which generates electrical impulses along lines 104 to a series of electrodes 105 which are described in further detail below. In the preferred embodiment, the stimulator 102 is operated by a battery 104 and encapsulated in a miniaturized package 106 constructed of a biocompatible material, permitting the device to be implanted under the skin.

A controller 110, which coordinates overall operation of the device, may be interconnected to a memory 112 for storing output parameters such as pulse frequency, pulse width, or pulse amplitude for a particular patient. Although the memory 112 may be backed-up with battery 104, in the preferred embodiment a non-volatile technology such as an electrically erasable programmable read-only memory (EEPROM) is used to retain the parametric data in the event that the battery needs to be changed. The controller 110 may be of conventional design, such as the 80C series or equivalent, which is available from the Intel Corp. of Santa Clara, Calif.

The preferred apparatus further includes an interface 108 interconnected to the controller 110, which enables the device to be coupled to programming apparatus 112 prior to implantation. Preferably, the programming apparatus 112 is in the form of a personal computer equipped with an appropriate interface and software enabling the nerve depolarization impulses to be viewed on the screen accompanying the computer and preset for a particular patient in terms of pulse frequency, pulse width, and pulse amplitude.

This adjustment prior to implantation may be based upon feedback from the patient, for example, in terms of affected area and/or pain level. Alternatively, an optional input device 120 may be used in conjunction with electrodes 122. The electrodes 122 may be temporarily implanted and used to sense myoelectrical activity of the surrounding muscles and, based upon the sensed information, adjustments may be made with respect to the output signals. As an alternative, the stimulator itself would incorporate inputs 130 to sense the myoelectrical activity of the surrounding muscles, and this information would be used to modulate the electrical output on an on-demand basis. In either case, the sensing electrode would preferably be implanted in a muscle of the neck or back to detect the myoelectric activity.

The electrodes 106 used for the actual stimulation of the medial branch are preferably composed of a material that conducts electricity, while being covered with a material throughout its length to prevent the spread of the current from the entire length of the electrode. In a preferred embodiment, such an electrode comprises a platinum wire coated with teflon, wherein the distal 2 mm of the tip is denuded of teflon, thereby creating a site for depolarization at the tip of the electrode.

The electrodes 106 would be provided in positive/negative pairs, with the positive lead being preferably placed at a distance of two centimeters or more from the negative lead. Depending upon the configuration, a single positive lead may be used in conjunction with a plurality of negative leads.

Figure 2:
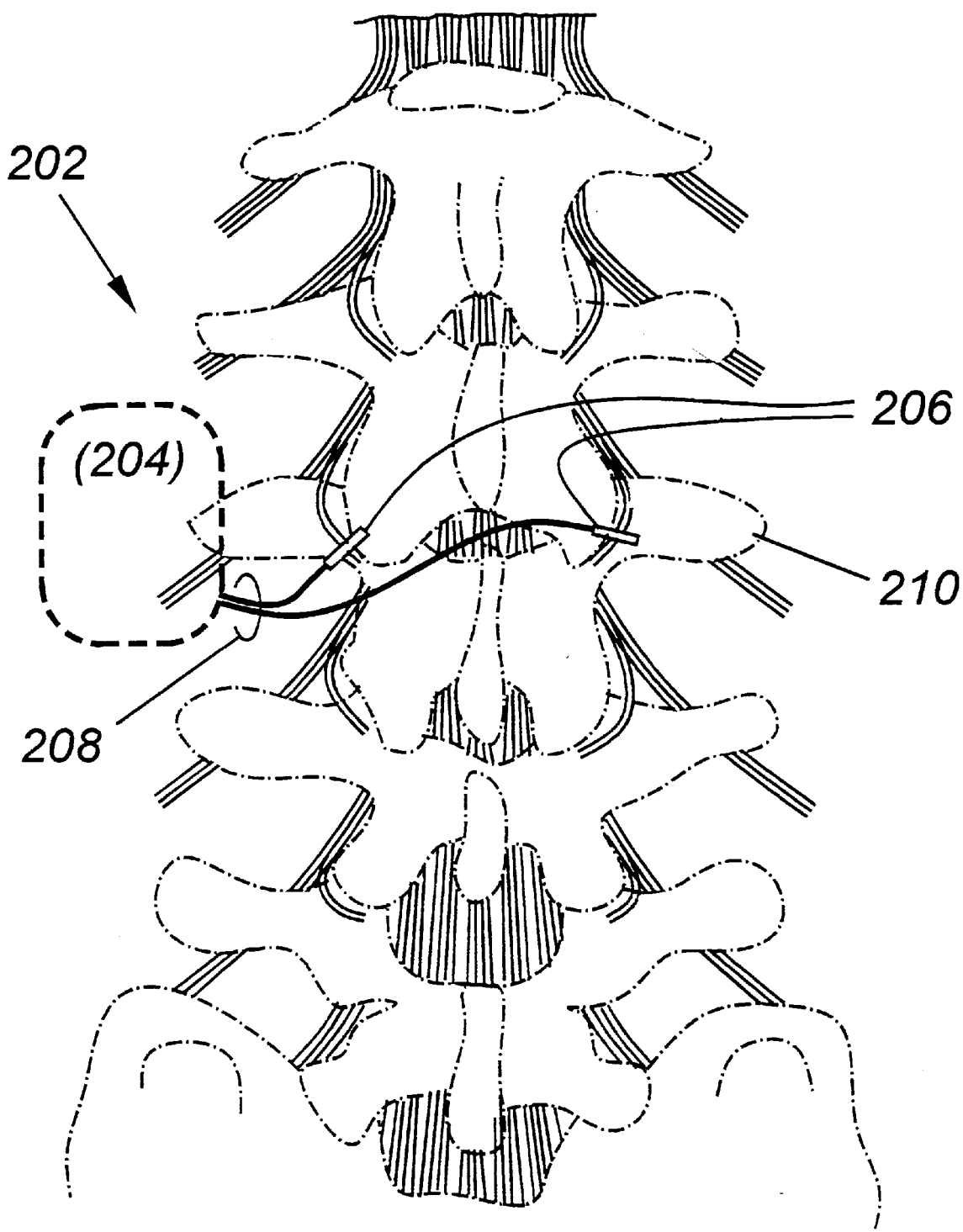
FIG. 2 is a drawing which shows the lower lumbar region of a patient destined to receive the inventive medial branch stimulator and electrode placement.

FIG. 2 is a drawing which shows generally at 202 the lower lumbar region of a patient destined to receive the inventive medial branch stimulator 204 and electrode placement. The distal tips 206 of the various leads are then placed near the medial branch 210 of the spinal nerve 212. In the event that multiple medial branch nerves require stimulation, additional are provided, as necessary. FIG. 3 illustrates a preferred electrode placement as seen from a side-view perspective.

The subcutaneous placement of the stimulator could be similar to the implantation of cardiac pacemakers. The subcutaneous placement of the electrodes would be performed under fluoroscopic guidance and with the use of a needle through which the electrode would be threaded.

I claim:

1. Apparatus for relieving zygopophysial joint related pain, comprising:

a stimulator coupled to a plurality of electrodes, each electrode being adapted for placement immediately adjacent to a medial branch of a spinal nerve root, the stimulator including:
a controller operative to generate a series of pulses of sufficient electrical intensity to cause depolarization of a given medial branch and its articular branches, but not so strong as to cause depolarization of the spinal cord itself, and operator interface enabling the series of pulses to be tailored as a function of requisite pain relief; and a second set of electrodes for sensing myoelectrical activity generated by the muscles surrounding the medial branch, the controller being programmed to modulate the impulses generated by the stimulator in accordance with the demands of the individual.

2. The apparatus of claim 1, wherein the stimulator is sealed within an enclosure suitable for implantation.

3. A method of relieving zygopophysial joint related pain, comprising the steps of:

providing a stimulator coupled to a plurality of electrodes;

placing each electrode immediately adjacent to a medial branch of a spinal nerve root; and generating a series of pulses sufficient to depolarize the medial branch and its articular branches, but not so intense as to depolarize of the spinal cord itself.

4. The method of claim 3, further including the step of tailoring the pulses to suit the demands of a user of the stimulator.

5. The method of claim 3, further including the steps of:

sensing the myoelectrical activity generated by the muscles surrounding the medial branch, and tailoring the pulses in accordance with the myoelectrical activity.

6. The method of claim 3, further including the step of implanting the stimulator beneath the skin.

7. The method of claim 3, further including the step of placing the electrodes subcutaneously.

* * * * *